US00PP11579P

United States Patent [19]

Griffith, Jr.

[11] Patent Number: Plant 11,579

[45] Date of Patent: Oct. 17, 2000

[54] COLEUS PLANT NAMED 'MILLENNIUM RED'

[75] Inventor: George W. Griffith, Jr., Gainesville, Fla.

[73] Assignee: Hatchett Creek Farms, Inc., Gainesville, Fla.

[21] Appl. No.: 09/222,278

[22] Filed: Dec. 28, 1998

[51] Int. Cl.[7] ..... A01H 5/00

[52] U.S. Cl. ..... Plt./373

[58] Field of Search ..... Plt./373, 263

*Primary Examiner*—Howard J. Locker
*Assistant Examiner*—Kent L. Bell
*Attorney, Agent, or Firm*—C. A. Whealy

[57] ABSTRACT

A distinct cultivar of Coleus plant named 'Millennium Red', characterized by its symmetrical, outwardly spreading, and mounded plant habit; red-purple and maroon bi-colored leaves with red-purple in center surrounded by deep maroon with a very narrow green margin; lack of flower development; excellent garden performance and tolerance to high temperatures and full sun conditions.

1 Drawing Sheet

BACKGROUND OF THE INVENTION

The present invention relates to a new and distinct cultivar of Coleus plant, botanically known as *Coleus×hybridus,* and hereinafter referred to by the cultivar name 'Millennium Red'. The new Coleus is marketed under the trade name Solar Millennium Red.

The new Coleus was discovered by the Inventor in Gainesville, Fla., as a naturally-occurring lateral branch mutation of a plant of the nonpatented *Coleus×hybridus* cultivar 'Solar Red' in 1996.

Asexual reproduction of the new cultivar by terminal and stem cuttings taken at Gainesville, Fla. has shown that the unique features of this new Coleus are stable and reproduced true to type in successive generations.

SUMMARY OF THE INVENTION

Plants of the cultivar 'Millennium Red' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Millennium Red'. These characteristics in combination distinguish 'Millennium Red' as a new and distinct cultivar:

1. Symmetrical, outwardly spreading, and mounded plant habit.

2. Red-purple and deep maroon bi-colored leaves with red-purple in center surrounded by deep maroon with a very narrow green margin. Red-purple and deep maroon areas of varying size and shape depending on light levels.

3. Lack of flower development.

4. Excellent garden performance; tolerant to high temperatures and full sun condition.

5. Less susceptible to bacterial pathogens common to Coleus.

Plants of the cultivar 'Millennium Red' can be compared to plants of the parent cultivar, the nonpatented *Coleus× hybridus* cultivar 'Solar Red'. Leaves of plants of the new Coleus are red-purple and deep maroon whereas leaves of plants of the parent cultivar are green and maroon. Additionally, in side-by-side comparisons conducted in Gainesville, Fla., plants of the new Coleus were taller and had larger leaves than plants of the parent cultivar.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of the new Coleus grown in a one-liter container under outdoor cultivation. Foliage colors in the photograph may appear lighter than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown in one-liter containers under outdoor production conditions during the summer and autumn in Gainesville, Fla., and Keller, Tex.

Botanical classification: *Coleus×hybridus* cultivar 'Millennium Red'.

Parentage: Naturally-occurring branch mutation of *Coleus× hybridus* cultivar 'Solar Red', not patented.

Propagation:

*Type cutting.*—Terminal and stem cuttings.

*Time to initiate roots.*—Summer: About 4 days at temperatures of about 29° C. Winter: About 4 days at temperatures of about 21° C.

*Time to develop roots.*—Summer: About 21 days at temperatures of about 35° C. Winter: About 28 days temperatures of about 24° C.

*Rooting habit:*—Numerous and fine.

Plant description:

*Type.*—Annual succulent herb in temperate regions; may be perennial in subtropical and tropical regions. Typically grown as container or garden plants.

*Crop time.*—From cuttings, about 12 weeks are required to produce a fully-grown finished plant in a one-liter container.

*Form.*—Symmetrical, outwardly branching and spreading; mounded. Appropriate for one-liter and smaller containers.

*Branching habit.*—Although very freely branching, pinching (removal of apices) will enhance branching; lateral branches may potentially form at every node.

*Plant height (from soil level to top of plant plane).*—About 24 cm.

*Area of spread.*—About 23 cm.

*Vigor.*—Moderate.

*Branches.*—Diameter: About 5 cm. Internode length: About 2.25 cm. Shape: Square in cross-section. Strength: Strong. Texture: Very minute hairs. Color: Green, close to 148A, with occasional reddish overtones.

*Foliage description.*—Leaves simple, generally symmetrical, opposite and long persisting. Length: About 5.7 cm. Width: About 3.9 cm. Aspect: Mostly horizontal. Shape: Ovate. Apex: Acute. Base: Obtuse. Margin: Crenate. Texture: Velvety, minute hairs on both surfaces. Color: Center typically red-purple surrounded by deep maroon outer area with a narrow green margin. Narrow green leaf margin usually only evident on margin scalloped edges. Actual patterns and relative areas of red-purple and deep maroon depend on light level; deep maroon areas more dominant with increased light level. Young and mature foliage, upper surface: Center, red-purple, 61A; area surrounding center, deep maroon, 187A; narrow outer margin, less than 1 mm wide and usually only evident on margin scalloped edges, green, 144A. Young and mature foliage, lower surface; Center, red-purple, 61A; area surrounding center, deep maroon, 187A; red-purple and deep maroon areas dulled compared to upper surface. Narrow green margin not typically observed. Venation, upper surface: Same as ground colors. Venation, lower surface: Pink. Petiole: Length: About 2.1 cm. Diameter: About 1.5 mm. Color: Light greenish pink.

Flower description: Flowers have not been observed to date on plants of the new Coleus.

Weather tolerance; Plants of the new coleus have exhibited good tolerance to high temperatures and full sun conditions; excellent garden performance.

Disease resistance: Under commercial conditions, plants of the new Coleus are less susceptible to bacterial diseases common to Coleus.

It is claimed:

1. A new and distinct cultivar of Coleus plant named 'Millennium Red', as illustrated and described.

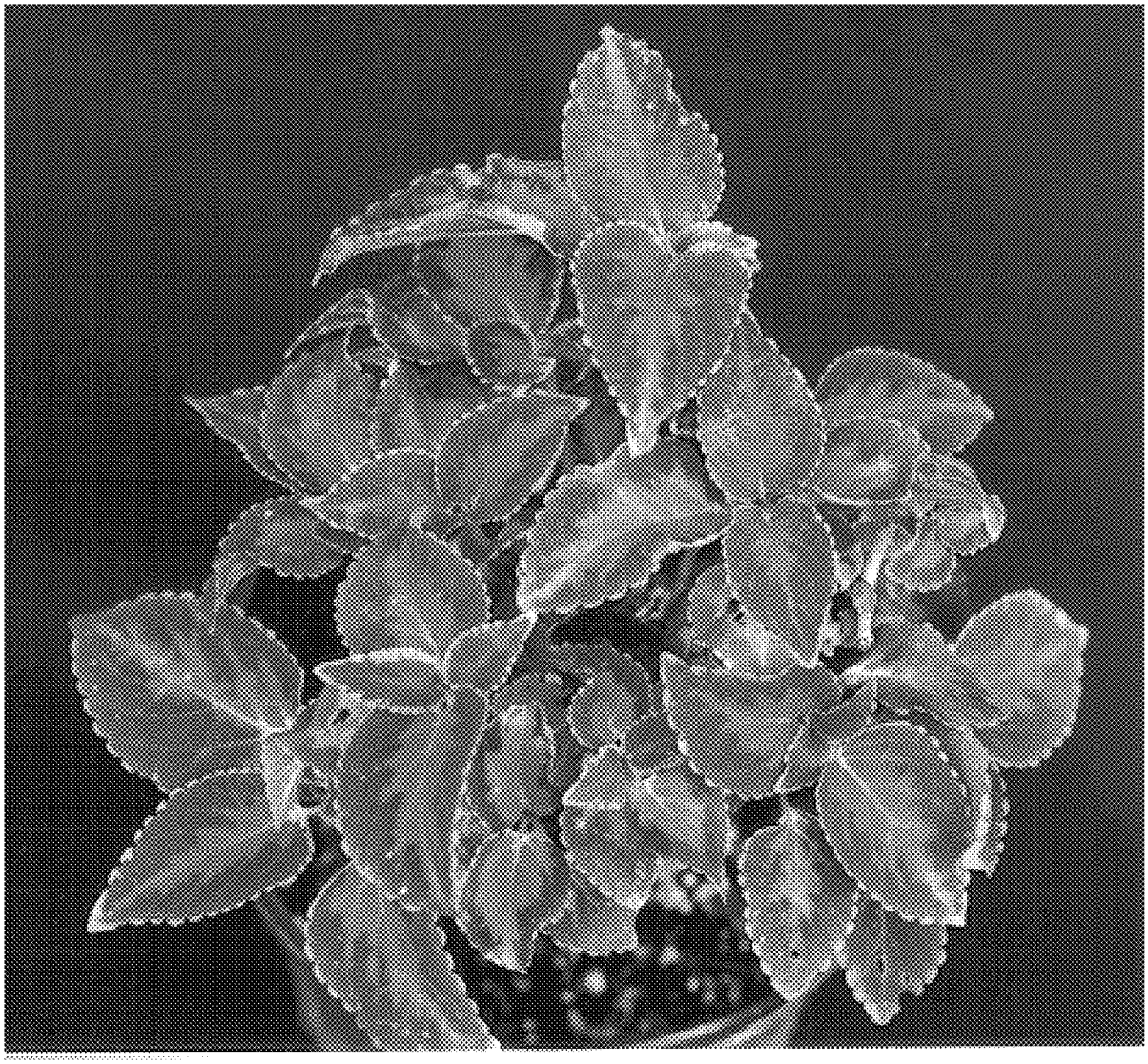

* * * * *